US012551365B2

(12) United States Patent
Stroebech

(10) Patent No.: US 12,551,365 B2
(45) Date of Patent: Feb. 17, 2026

(54) APPLICATION AID FOR OSTOMY DEVICE

(71) Applicant: Coloplast A/S, Humlebaek (DK)

(72) Inventor: Esben Stroebech, Hoersholm (DK)

(73) Assignee: Coloplast A/S, Humlebaek (DK)

( * ) Notice: Subject to any disclaimer, the term of this patent is extended or adjusted under 35 U.S.C. 154(b) by 1031 days.

(21) Appl. No.: 17/637,814

(22) PCT Filed: Aug. 27, 2020

(86) PCT No.: PCT/DK2020/050240
§ 371 (c)(1),
(2) Date: Feb. 24, 2022

(87) PCT Pub. No.: WO2021/037321
PCT Pub. Date: Mar. 4, 2021

(65) Prior Publication Data

US 2022/0280331 A1 Sep. 8, 2022

(30) Foreign Application Priority Data

Aug. 28, 2019 (DK) ........................... PA 2019 70536

(51) Int. Cl.
*A61F 5/443* (2006.01)
*A61F 5/44* (2006.01)
*A61F 5/449* (2006.01)

(52) U.S. Cl.
CPC ............ *A61F 5/443* (2013.01); *A61F 5/4401* (2013.01); *A61F 5/449* (2013.01)

(58) Field of Classification Search
CPC ........ A61F 5/445; A61F 5/443; A61F 5/4401; A61F 5/4404; A61F 5/448; A61F 5/449;
(Continued)

(56) References Cited

U.S. PATENT DOCUMENTS 2,869,548 A 1/1959 Mason
3,906,951 A * 9/1975 Chen .................... A61L 28/008
604/336
(Continued)

FOREIGN PATENT DOCUMENTS

AU 2011247843 B2 6/2014
CA 2517997 C 12/2013
(Continued)

*Primary Examiner* — Nicholas J. Weiss
*Assistant Examiner* — Gabriella E Burnette
(74) *Attorney, Agent, or Firm* — Coloplast Corp., Coloplast A/S; Nick Baumann

(57) ABSTRACT

Application aid (10) adapted to assist a user in applying an adhesive base plate (20) of an ostomy appliance to a skin surface around a stoma of the user, the adhesive base plate comprising a first adhesive surface (30) facing the skin and a second surface ((40) facing away from the skin, the application aid is configured to be removably attached to the base plate and adaptable to at least partly surround the stoma of the user during application of the base plate to the skin surface around the stoma of the user, the application aid comprising a substrate component (70) and a protective component (80) provided on one surface of the substrate component and adapted to prevent mucus from the mucous membrane of the stoma to contaminate the base plate by mucus during application of the base plate to the skin surface around the stoma of the user.

12 Claims, 3 Drawing Sheets

(58) Field of Classification Search
CPC ...... A61F 2005/4402; A61F 2005/4455; A61F 5/4407; A61F 5/4408
See application file for complete search history.

(56) References Cited

U.S. PATENT DOCUMENTS

| | | | | |
|---|---|---|---|---|
| 4,187,850 | A * | 2/1980 | Gust | A61F 5/445 604/338 |
| 5,071,690 | A | 12/1991 | Fukuda et al. | |
| 5,496,296 | A * | 3/1996 | Holmberg | A61F 5/443 604/336 |
| 6,409,709 | B1 * | 6/2002 | Recto | A61F 5/445 604/338 |
| 6,569,081 | B1 | 5/2003 | Nielsen et al. | |
| 12,121,470 | B1 * | 10/2024 | Kelly | A61F 5/443 |
| 2004/0260256 | A1 | 12/2004 | Ciok et al. | |
| 2005/0033249 | A1 * | 2/2005 | Whiteford | A61F 5/448 604/338 |
| 2010/0145292 | A1 | 6/2010 | Mayer | |
| 2011/0172619 | A1 | 7/2011 | Argent | |
| 2017/0156917 | A1 | 6/2017 | Guidry et al. | |
| 2020/0046542 | A1 * | 2/2020 | Guidry | H05B 1/025 |

FOREIGN PATENT DOCUMENTS

| | | | |
|---|---|---|---|
| CN | 1251980 | C | 4/2006 |
| CN | 201320237 | Y | 10/2009 |
| CN | 201370671 | Y | 12/2009 |
| CN | 203777128 | U | 8/2014 |
| CN | 107530181 | B | 11/2020 |
| CN | 108135725 | B | 1/2021 |
| CN | 109414338 | B | 9/2021 |
| CN | 109640897 | B | 10/2021 |
| DK | 200100141 | A | 7/2002 |
| GB | 2041753 | A | 9/1980 |
| GB | 2425482 | A | 11/2006 |
| GB | 2491161 | A1 | 11/2012 |
| JP | 3159727 | A2 | 7/1991 |
| WO | 08013511 | A1 | 1/2008 |
| WO | 2010121623 | A1 | 10/2010 |
| WO | 11070372 | A1 | 6/2011 |
| WO | 11070373 | A1 | 6/2011 |
| WO | 17037450 | A1 | 3/2017 |

* cited by examiner

APPLICATION AID FOR OSTOMY DEVICE

BACKGROUND

Stomal output often contains body fluids and visceral contents that are aggressive to both the skin of a user and to ostomy devices, in particular these have a detrimental effect on the efficiency and integrity of the adhesive materials that are applied to attach the ostomy device to the user's skin surface. Some ostomists may choose or have to wear their device for prolonged periods of time. For users in general, and particularly for these ostomists safe, reliable and efficient ostomy devices are highly desirable. Numerous attempts have been made to provide ostomy devices to meet the such demands, e.g. the demand of prolonged wear time, but the provision of sufficient efficiency to achieve a satisfactory long wear time of ostomy devices continues to be an unmet need.

Ostomists and health care professionals alike would welcome improvements in ostomy devices to better meet such demands.

SUMMARY

The present disclosure provides aspects of an application aid adapted to assist a user in applying an adhesive base plate of an ostomy appliance to a skin surface around a stoma of the user without contaminating the adhesive base plate, according to the appended claims.

BRIEF DESCRIPTION OF THE DRAWINGS

The accompanying drawings are included to provide a further understanding of embodiments and are incorporated in and constitute a part of this specification. The figures illustrate embodiments and together with the description serve to explain principles of embodiments. Other embodiments and many of the intended advantages of embodiments will be readily appreciated as they become better understood by reference to the following detailed description. Like reference numerals designate corresponding similar parts.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and may be practiced in any other embodiments even if not so illustrated, or if not so explicitly described.

Figure 1:
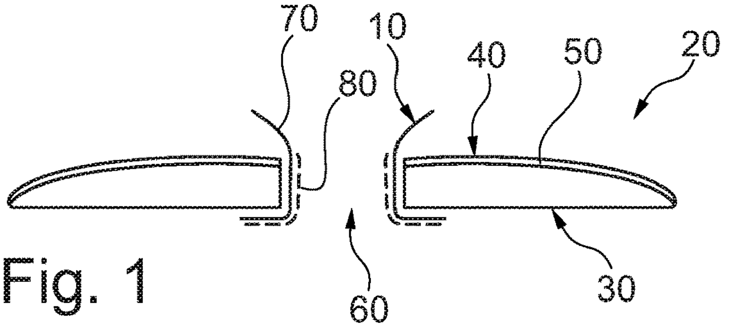
FIG. 1 is a schematic cross-section view of one embodiment of an application aid arranged at a base plate.

FIGS. *8a* and *8b* are showing spreading of a droplet when squeezed between glass plates.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized, and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output," "waste(s)," and "fluids" interchangeably. A subject having undergone ostomy surgery may be referred to as "ostomist" or "ostomate"-moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side of a device or part of a device, the referral is to the skin-facing side, when the ostomy appliance is worn by a user. Likewise, whenever referring to the distal side of a device or part of a device, the referral is to the side facing away from the skin, when the ostomy appliance is worn by a user. In other words, the proximal side is the side closest to the user, when the appliance is fitted on a user and the distal side is the opposite side—the side furthest away from the user in use.

The axial direction is defined as the direction of the stoma, when the appliance is worn by a user. Thus, the axial direction is generally perpendicular to the skin or abdominal surface of the user.

The radial direction is defined as transverse to the axial direction that is transversely to the direction of the stoma. In some sentences, the words "inner" and "outer" may be used. These qualifiers should generally be perceived with reference to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the phrase "substantially" as a qualifier to certain features or effects in this disclosure is intended to simply mean that any deviations are within tolerances that would normally be expected by the skilled person in the relevant field.

In one aspect, the present disclosure relates to an application aid adapted to assist a user in applying an adhesive base plate of an ostomy appliance to a skin surface around a stoma of the user, the adhesive base pate comprising a first adhesive surface facing the skin and a second surface facing away from the skin, the application aid is configured to be removably attached to the base plate and adaptable to at least partly surround the stoma of the user during application of the base plate to the skin surface around the stoma of the user, comprising: a substrate component comprising a first surface configured to locate in a direction away from the peristomal skin and/or away from the stoma, and a second surface configured to locate in a direction towards the peristomal skin and/or towards the stoma; and a protective component provided on the second surface of the substrate component and adapted to prevent mucus from the mucous membrane of the stoma to contaminate the base plate by mucus during application of the base plate to the skin surface around the stoma of the user; wherein at least a portion of the first surface of the substrate component is configured to engage a peripheral edge of a stoma-receiving opening in the base plate.

During application of a base plate to the skin around a stoma, great care must be taken not to contaminate the adhesive surface of the base plate with mucus from the mucous membrane of the stoma and/or with effluents (stomal waste) from the stoma. However, particularly with respect to avoiding mucus from contaminating the adhesive of the base plate, it has been experienced that this may be difficult to avoid. Moreover, investigations show that users are much less attentive to avoiding mucus than they are of avoiding stomal effluents when applying the base plate. The aperture in the base plate is cut to fit around the stoma thus leaving very little extra space around it during application. The risk of touching the stoma with the edge of the base plate during application is high and even a small droplet of mucus will spread to wet (contaminate) a substantial area of the adhesive surface when the base plate is subsequently pressed against the skin surrounding the stoma. All stomas have individual sizes and shapes deviating between them, making the task of avoiding contamination of the adhesive surface of the base plate even more difficult. Furthermore, it is often difficult for the user to see what he or she is doing when applying the base plate to their belly.

When mucus enters the adhesive surface of the base plate, the adhesive tack of the adhesive can decrease temporarily or permanently, thereby creating room/channels for the leakage may already have started by then and damage is done.

Figure 8A:
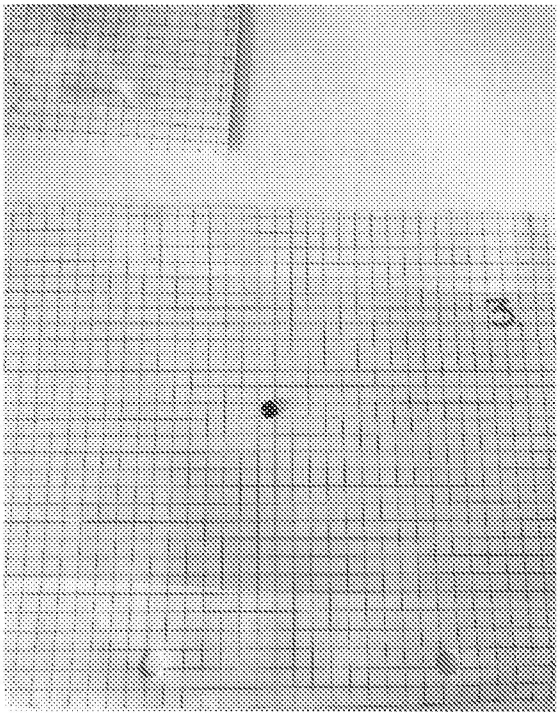
Figure 8B:
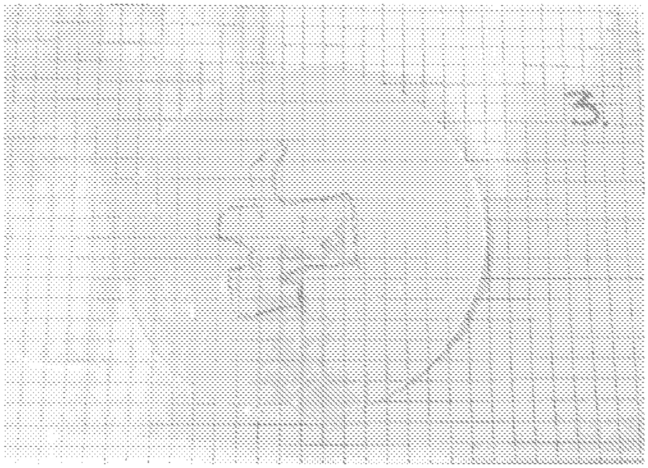

Even a tiny little droplet of mucus on the adhesive surface may cause substantial damage. This is illustrated in FIGS. 8*a*-8*b*, where a droplet of coloured liquid (illustrating mucus, and coloured in order to enhance visibility) is placed on a glass plate (illustrating the skin). In FIG. 8*b*, a second glass plate (illustrating a base plate) is placed over the droplet, and the droplet is thereby squeezed and spread over a larger area. The contours of the spread droplet are drawn up to visualize the area now being contaminated with liquid. As can be seen, the droplet of liquid is now squeezed out to cover a substantial portion of the glass plate. It is believed that the same mechanism applies on the adhesive surface of a base plate having been subjected to a splash of mucus on it, when it is applied to the skin surface around a stoma. Thereby, the adhesive can be "damaged" or "weakened" already from the attachment of the fresh base plate which is likely to reduce the total wear time of the base plate.

Addressing stoma herein refers to both ostomy, iliostomy and urostomy as the problem of contamination of the adhesive surface of the base plate may occur in these conditions.

In aspects, the application aid facilitates safe application of a base plate around a stoma by decreasing or eliminating the risk of contamination of the adhesive during application by eliminating the possibility of mucus (stoma juice) to contaminate the periphery of the stoma-receiving opening and the adhesive surface of the base plate, as well as removing the almost invisible seeped-out stoma juice on the near peristomal skin before the adhesive base plate is brought into contact with the skin.

In embodiments, the substrate component can comprise a neck portion extending axially outwards from the peripheral edge of the stoma receiving opening. The neck portion may be substantially concentric to the stoma. In embodiments the neck portion is broader at a distal end than at a proximal end. In embodiments, the neck portion may have a substantially circular cross-section. In embodiments, the neck portion extends as a tube around the stoma or it may be in the form of one or more (separate) strips extending in axial direction. In embodiments, the neck portion has a cross-section that is configured to adapting to the shape of the peripheral edge of the stoma receiving opening. The neck portion can protect the base plate from direct contact with the stoma as well as it can protect the stoma from direct contact with the surroundings during application. In embodiments, the neck portion is partly or fully lining the peripheral edge of the stoma receiving opening of the base plate. In embodiments, the neck portion is encircling the stoma, and comprises an axial cut-out allowing the neck portion to be adapted to a larger or smaller diameter of the stoma.

In embodiments, the neck portion has a height, measured from the stoma receiving opening and axially outwards, of at least 1 mm, such as at least 5 mm, such as at least 10 mm. In embodiments, the height of the neck portion is 1-70 mm, such as 1-60 mm, such as 1-50 mm, such as 5-40 mm, such as 8-30 mm, such as 10-25 mm. In embodiments, the height of the neck portion is at least equal to a thickness of the base plate.

In embodiments, the neck portion of the substrate component comprises a tab member for easing removal of the application aid by pulling on the tab member. In embodiments, the tab may be an outwardly extending part of the substrate component. In embodiments, the tab is in the form of a ring configured for inserting a finger therethrough.

In embodiments, the substrate component comprises a foot portion extending radially outwards from the peripheral edge of the stoma receiving opening. In embodiments, the foot portion extends from a first end portion of the substrate component and towards the periphery of the stoma receiving opening. In embodiments, the foot portion is located on the proximal side of the base plate, serving to at least protect the adhesive surface of the base plate closest to the stoma receiving opening.

In embodiments, the foot portion of the substrate component is extending over a portion of the first adhesive surface of the base plate. Hence, the foot portion is capable of protecting the adhesive surface against contamination with mucus from the mucous membrane of the stoma during application. In embodiments, a distal surface of the foot portion comprises a release surface. By release surface is meant a surface that is easily released from an adhesive, for example a siliconized surface. Such surface allows for easy detachment of the substrate component/foot portion from the adhesive surface of base plate when the substrate component is to be removed.

In embodiments, the substrate component comprises one or more strips. In embodiments, the strip(s) comprise(s) a sheet material cut into one or more strips. In embodiments, the strips are aligned in axial direction. In embodiments, the strip(s) are folded, with a first strip portion configured to be located in a direction away from the peristomal skin and/or away from the stoma, defining the first surface of the substrate component, and a second strip portion configured to be located in a direction facing towards the peristomal skin and/or towards the stoma, defining the second surface of the substrate component and a folding line at the foot portion. Such construction may facilitate that the one or more strips will conduct a rolling motion when a neck end of the second strip portion is pulled, thereby removing the strip from the adhesive surface by rolling. In embodiments, the strips are connected to each other to form a single sheet at the neck portion, but are separate, forming two or more discreet strips at the foot portion.

In embodiments, the strip(s) comprises one or more pulling tabs. In embodiments, the second strip portion is provided with a pulling tab at the neck portion, extending further than the first strip portion to allow easy gripping of the tab.

In embodiments, the strip(s) are broader at the foot portion than at the neck section. This facilitates that the foot portion covers a larger portion of the adhesive surface near the stoma receiving opening.

A protective component is provided on the second surface of the substrate component. The protective component can cover the second surface entirely or only partly. In embodiments, the protective component comprises absorbent material. The protective component can comprise an absorbent net, fabric, paper, tissue, textile or non-woven. In embodiments, the protective component comprises an absorbent powder or coating. Examples of suitable powders or coatings are hydrocolloids such as, but not limited to, CMCs (carboxy methyl celluloses). In embodiments, the absorbent powder is dusted onto the second surface of the substrate component. In embodiments, the protective component is lined, layered, sprayed or dusted onto the second surface of the substrate component. In embodiments, the protective component comprises a “hairy” surface.

The protective component is capable of absorbing stomal juice or mucus that enters the second surface of the application aid. Furthermore, when stomal juice or mucus have been seeping from the stoma and wetted the skin around the stoma—potentially just creating a thin and almost invisible layer, but still enough to compromise the adhesive—this layer can be absorbed by the protective component and thereby removed and is unable to disturb or damage the adhesive surface of the base plate.

In embodiments, the protective component is located on the second surface of the foot portion of the substrate component. In embodiments, the protective component is also provided on the neck portion.

In embodiments, the protective component is provided on the neck portion of the substrate component.

In embodiments, at least a part of the substrate component is pleated. The pleats allow for compressing the substrate component in the neck portion, whereas the pleats can be more flattened out in the foot section.

In embodiments, the length of the foot portion is 1-20 mm, such as 1-10 mm, extending over the adhesive surface of the base plate, measured from the peripheral edge of the stoma receiving opening and radially outwards.

In embodiments, the substrate component is formed by a film material, a foil material, a non-woven material, a fabric material or a paper material. In embodiments, the substrate component is a flexible sheet material having sufficient stiffness to stay in shape but at the same time sufficient softness to be bent around (the edge of) the peripheral edge of the stoma receiving opening. In embodiments, the substrate component comprises elastic material.

In aspects, the present disclosure relates to a kit of parts, comprising the application aid of claim 1 and an adhesive base plate, wherein the application aid is an accessory component to be combined with the base plate before or during application of the base plate to the skin.

When an ostomy base plate is prepared for application to the peristomal skin, the opening size is chosen or adjusted to the contour of the ostomy. The user is instructed in cutting the opening in a shape such that the adhesive of the base plate will only adhere to the skin (not the stoma) and leave a 1 mm boundary of skin before the mucus membrane (stoma) starts. As the opening in the base plate have to be only slightly bigger that the size of the stoma, in order to avoid damage to the peristomal skin from moisture (maceration) or aggressive output (enzymes), contamination of the adhesive before bonding to the skin may unintentionally occur. This has been found to happen often as the inner opening perimeter of the opening of the base plate will touch and “scrape off” the stoma juice (mucin and water) when moving the adhesive base plate toward the skin for bonding. It has further been found that in some cases, an almost invisible layer of mucus or stoma juice is already present at the root of the stoma and/or near the peristomal skin. This layer of mucus should be removed in order to get a good bonding of the base plate to the skin.

In embodiments, the application aid is provided as an integrated part of a base plate, in the sense that the base plate is delivered with the application aid mounted. After application, the application aid is removed.

In embodiments, the application aid is a separate component that can be applied to a base plate before use. The application aid can be a single use product, or it can be possible to reuse the application aid with a fresh base plate, e.g. after cleaning of the application aid.

The application aid can be applicable for use in both 1-piece and 2-piece ostomy devices. In embodiments of a 1-piece ostomy device, the application aid can be configured to be removed from the base plate and to enter into the collecting bag. In 2-piece device embodiments, the application aid can be removed before attaching the collecting bag to the base plate.

In embodiments, the application aid is a two-part system where one or more parts can be exchanged. For example, the protective component can be exchangeable facilitating reuse of the substrate component.

In embodiments, the application aid surrounds the stoma but optionally the application aid is cut open in such a way that it can adapt to fit any size and shape of a stoma.

In embodiments, the invention relates to a kit of parts, comprising the application aid of claim 1 and an adhesive base plate, wherein the application aid is an accessory component to be combined with the base plate before or during application of the base plate to the skin.

Embodiments relate to a method for preventing contamination of an adhesive surface of an ostomy base plate during application comprising the steps of:

a. Providing an application aid according to the disclosure
b. Providing an adhesive base plate
c. Arranging the application aid on the base plate
d. Applying the base plate to the skin around a stoma and
e. Removing the application aid.

Embodiments further relate to a method for preventing contamination of an adhesive surface of an ostomy base plate during application comprising the steps of:

a. Providing an application aid according to the disclosure
b. Providing an adhesive base plate
c. Arranging the application aid on the skin surrounding a stoma
d. Applying the base plate to the skin and fit the opening of the base plate around the application aid and
e. Removing the application aid.

When applying the base plate to the skin around a stoma, the base plate is positioned with the stoma aligned with the opening and then brought into contact with the skin surrounding the stoma and leaving the stoma to protrude through the opening. As the opening in the base plate typically is only slightly larger than the stoma, it can be difficult, if not impossible to position the base plate without having the plate touching the stoma. Even a small drop of mucus has been found to be able to compromise the adhesive tack of the adhesive. To align and apply the base plate without mucus entering the adhesive surface demands high dexterity, good view (which can be impaired by the belly) and plenty of luck. The application aid may reduce the risk of contamination of the base plate adhesive by providing protection of the adhesive surface surrounding the opening.

DETAILED DESCRIPTION OF THE DRAWINGS

FIG. 1 is showing an embodiment of an application aid (10) mounted on a base plate (20). The base plate comprises a first skin-facing adhesive surface (30) and a second surface (40) facing away from the skin. The second surface (40) is typically provided with a backing layer (50) and means for attachment of a collecting bag (not shown). The base plate (20) is provided with a stoma-receiving opening (60). The application aid comprises a substrate component (70) facing away from the skin/stoma and a protective component (80) closest to the skin/stoma. During application of the base plate (20) to the skin, the stoma may touch the application aid (10)—or drip mucus on it—and this liquid will be removed, e.g., by absorbing or draining by the protective component (80) instead of being smeared over the adhesive surface (30). On the surface of the substrate component (70) facing the adhesive surface (30) is provided a release layer (not shown) facilitating easy release of the substrate component (70) from the adhesive layer (30) when the application aid (10) is to be removed.

Figure 2:
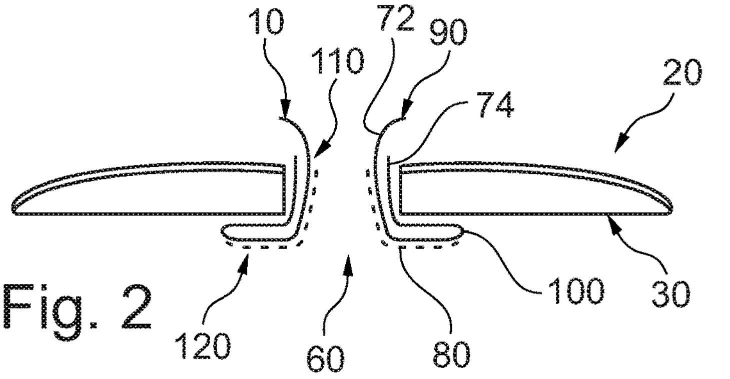
FIG. 2 is a schematic cross-sectional view of another embodiment of an application aid arranged at a base plate.

In FIG. 2 is shown an embodiment of an application aid (10) where the substrate component (72,74) is folded to constitute a double layer, folded (100) at the foot portion (120). The first layer (74) of the substrate component facing the adhesive surface (30) is overlying the second layer (72) facing towards the stoma and skin. At the neck portion (110), the second layer (72) is provided with a tab (90). When the base plate (20) has been applied to the skin surface of the user, the tab (90) can be pulled, and the application aid (10) is thereby "rolled" off and removed.

Figure 3:
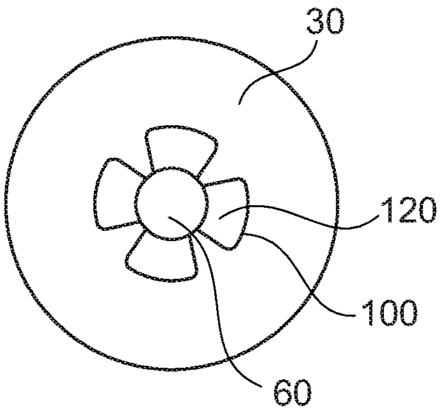
FIG. 3 and FIG. 4 show proximal views of embodiments of application aids comprising strips, arranged at a base plate.
Figure 4:
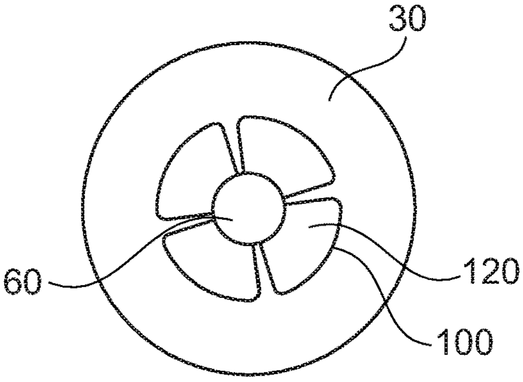

In FIGS. 3 and 4 are proximal views of embodiments of application aids wherein the substrate component comprises four strips (120), the strips being double layers with a folding line (100) on the foot portion, furthest away from the stoma receiving opening (60). The four strips (120) together does not cover the entire adhesive surface (30) near the stoma receiving hole (60), but they cover a large portion of the area and thus reduce the risk of contamination of the adhesive surface (30) significantly. In FIG. 3, the strips (120) has substantially the same width along the entire length of the strip, whereas in FIG. 4 is shown strips being broader at the foot portion, thereby covering a larger area of the adhesive surface.

Figure 5:
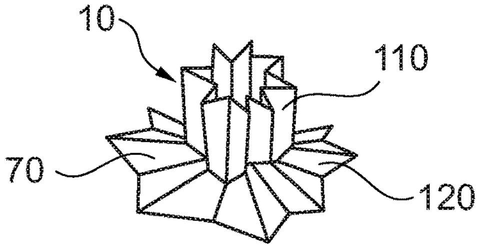
FIG. 5 show an embodiment of an application aid with a pleated substrate component.

FIG. 5 shown an embodiment of the application aid 10 where the substrate component (70) is pleated. The pleated structure facilitates easy adjustment to different sizes of stomas as well as different sizes and shapes of openings in the base plate. In embodiments, (not shown) the pleated structure is substituted with a helix structure capable of broadening or narrowing the substrate component or part thereof.

Figure 6:
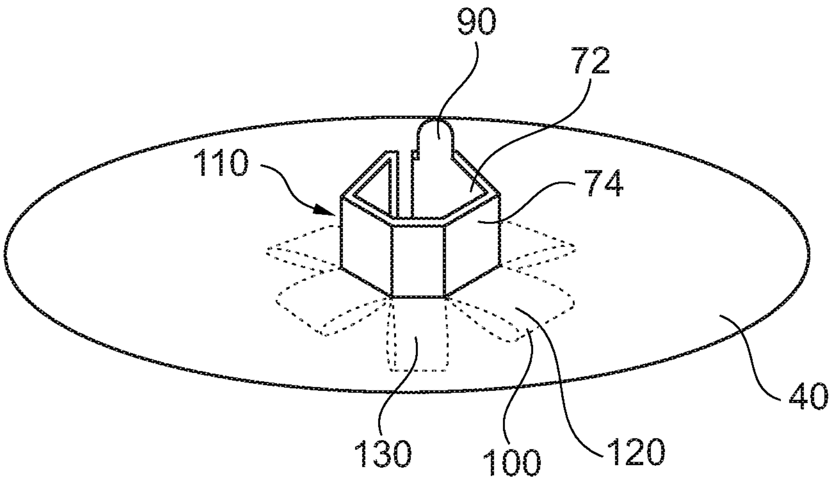
FIG. 6 shows an embodiment of an application aid where the foot portion is cut into strips, the application aid is arranged on a base plate.
Figure 7:
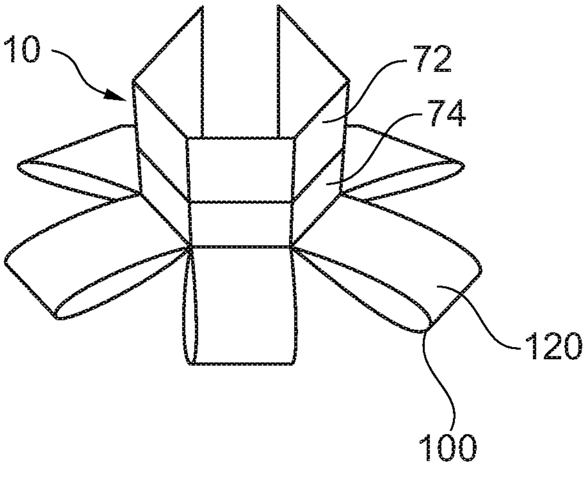
FIG. 7 an embodiment of an application aid where the foot portion is cut into strips.

In FIG. 6 is shown an embodiment where the substrate component (72,74) is in the form of a double layered sheet, being folded along a peripheral bending line (100) in the foot portion. The substrate component is provided with a tab (90) at the neck portion (110). The neck portion (110) is curved or bended into a rounded shape fitting in the aperture of the base plate. In the foot portion (120), here shown in broken lines as it is covered by the base plate in this view, the folded sheet has been cut into strips (130) allowing the strips (130) to extend radially over the adhesive surface of the base plate. In FIG. 7 is shown an application aid (10) before application to the base plate, the substrate component (70) being a folded sheet material being cut into slits in the foot portion (120).

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of body side members for ostomy appliances as discussed herein. Therefore, it is intended that this invention be limited only by the claims and the equivalents thereof.

The invention claimed is:

1. Application aid adapted to assist a user in applying an ostomy appliance having an adhesive surface attachable to a skin of a user around a stoma, the application aid comprising:

a substrate comprising a first distal surface configured to contact the ostomy appliance and a second proximal surface configured to contact the skin of the user and the stoma;

a release agent applied to the first distal surface, where the release agent is configured to not stick to the adhesive surface of the ostomy appliance; and a protective component provided on the second proximal surface of the substrate, where the protective component comprises an absorbent that is adapted to absorb and reduce mucous of the stoma from contaminating the adhesive surface of the ostomy appliance;

wherein the substrate is an accessory provided separate from the ostomy appliance;

wherein the substrate comprises a neck portion adapted to be located between the stoma and the ostomy appliance and a foot portion adapted to be located between the skin of the user and the adhesive surface of the ostomy appliance.

2. The application aid of claim 1, wherein the substrate further comprises a pull tab extending from the neck portion.

3. The application aid of claim 1, wherein the substrate is a folded substrate with a fold line formed on the foot portion, with a first portion of the folded substrate extending from the fold line to a first end of the substrate and a second portion of the folded substrate extending from the fold line to a second end of the substrate, with the first portion of the folded substrate providing the first distal surface of the substrate and the second portion of the folded substrate providing the second proximal surface of the substrate.

4. The application aid of claim 1, wherein the protective component is layered on the second proximal surface of the substrate.

5. The application aid of claim 1, wherein the protective component is sprayed on the second proximal surface of the substrate.

6. The application aid of claim 1, wherein the protective component is dusted on the second proximal surface of the substrate.

7. The application aid of claim 1, wherein the protective component comprises an absorbent powder.

8. The application aid of claim 1, wherein the foot portion has a width that is equal to a width of the neck portion of the substrate.

9. The application aid of claim 1, wherein the foot portion is wider than the neck portion of the substrate.

10. The application aid of claim 1, wherein the foot portion of the substrate comprises a plurality of petals, with each petal of the plurality of petals separated from an adjacent one of the plurality of petals by an open space.

11. The application aid of claim 1, wherein at least the neck portion of the substrate is pleated.

12. The application aid of claim 1, wherein the substrate comprises a paper material.

* * * * *